United States Patent [19]

Lochhead et al.

[11] Patent Number: 5,004,598

[45] Date of Patent: Apr. 2, 1991

[54] STABLE AND QUICK-BREAKING TOPICAL SKIN COMPOSITIONS

[75] Inventors: Robert Y. Lochhead, Avon Lake; Janet Y. Castaneda, Lorain; Wilfred J. Hemker, Berea, all of Ohio

[73] Assignee: The B. F. Goodrich Company, Akron, Ohio

[21] Appl. No.: 358,924

[22] Filed: May 31, 1989

Related U.S. Application Data

[63] Continuation-in-part of Ser. No. 928,755, Nov. 10, 1986, abandoned.

[51] Int. Cl.$^5$ .......................... A61K 7/15; A61K 7/42; A61K 7/44; A61K 7/50
[52] U.S. Cl. ........................................ 424/59; 424/60; 424/73; 514/846; 514/939
[58] Field of Search ...................... 424/59, 60; 514/938

[56] References Cited

U.S. PATENT DOCUMENTS

| | | | |
|---|---|---|---|
| 3,406,238 | 10/1968 | Freyermuth et al. | 424/59 |
| 3,529,055 | 9/1970 | Skoultchi et al. | 424/59 |
| 3,670,074 | 6/1972 | Doner | 424/60 |
| 3,784,488 | 1/1974 | Steinhauer et al. | 424/59 |
| 4,172,122 | 10/1979 | Kubik et al. | 424/59 |
| 4,421,902 | 12/1983 | Chang et al. | 424/81 |
| 4,552,755 | 11/1985 | Randen | 514/938 |
| 4,597,963 | 7/1986 | Deckner | 424/59 |

OTHER PUBLICATIONS

Polymers in Emulsification, Soap and Chemical Specialties, Apr.–May, 1961.
Effect of Neutralizing Amine on the Stability of Emulsions Prepared with Carboxy Vinyl Polymers, J. Soc. Cosmetic Chemists, vol. 20, pp. 215–223, Mar. 4, 1969.

*Primary Examiner*—Dale R. Ore
*Attorney, Agent, or Firm*—George A. Kap; Konrad H. Kaeding

[57] ABSTRACT

This invention relates to stable oil-in-water emulsions and to products based on such emulsions which contain a modified polymer which is a copolymer of a preponderant amount of an acrylic acid and a smaller amount of a long chain acrylate monomer which modified polymer renders the emulsions stable for over a year at room temperature and which imparts to the emulsions the quick breaking property whereby the emulsions break on coming in contact with an electrolyte or skin, instantaneously coalescing and releasing oil from the emulsions.

10 Claims, No Drawings

STABLE AND QUICK-BREAKING TOPICAL SKIN COMPOSITIONS

REFERENCE TO RELATED APPLICATION

This application is a continuation-in-part of application Ser. No. 928,755 filed Nov. 10, 1986, and entitled "Stable And Quick-Breaking Topical Skin Composition" now abandoned.

BACKGROUND OF THE INVENTION

An emulsion is defined as a macroscopic dispersion of two liquids--one of which forms the continuous phase of the system and the other forms the discontinuous or discrete phase. An emulsion of two liquids without a stabilizer will quickly break into two liquid layers.

Oil-in-water emulsions contain discrete droplets or particles of oil in a continuous water phase. Stability of such emulsions depends on the primary emulsifiers which emulsify and stabilize the oil droplets against coalescence. Secondary emulsifiers enhance the stabilizing property of the primary emulsifiers The secondary emulsifiers cannot by themselves emulsify and stabilize oil droplets against coalescence.

The use of the emulsion as a vehicle for skin preparations dates back to the invention of the first cold cream in about 150 A.D. The lotions or creams, in oil-in-water emulsion form, continue to this day to be the most popular delivery systems for applying functional cosmetics to the skin.

The effect of gravity on emulsions has long resulted in the general problem of sedimentation or creaming of the oil phase resulting in phase separation. It is a requirement of commercial emulsions that they should exhibit stability against such separation for extended periods of time, in some cases up to two years. Because of inability to cope with this handicap, many cosmetic products have failed at some stage of commercial development.

The prior art describes homopolymers of acrylic acids partially neutralized with long-chain alkylamines. Such homopolymers can function as primary emulsifiers or surfactants. Prior art emulsions prepared with a homopolymer of acrylic acid are not stable below pH of 5.7 when the homopolymer is neutralized with dodecylamine or below pH of 6.6 when the homopolymer is stabilized with n-hexylamine. It should be noted that pH of natural human skin is 5.5.

SUMMARY OF THE INVENTION

Oil-in-water emulsions and fully formulated cosmetic skin compositions based on the oil-in-water emulsions are prepared by admixing water, oil, a neutralizing agent, and a lightly crosslinked modified polymer containing a small amount of a long chain acrylate ester comonomer. The modified polymer can act as a primary emulsifier. In a preferred embodiment, such oil-in-water emulsions are also stable at pH of about less than 6 and break when they come in contact with an electrolyte, such as is found in the human perspiration on the skin. In a preferred embodiment, the skin compositions can be formulated in total absence of conventional surfactants.

DETAILED DESCRIPTION OF THE INVENTION

This invention relates to oil-in-water emulsions which are shelf-stable and which instantaneously break when they come in contact with a salt or an electrolyte. Such emulsions are especially useful in preparing topical cosmetic skin compositions wherein the emulsion breaks on contacting the electrolyte on the skin, thus allowing the coalescence of oil particles in the discontinuous phase. The oil so released functions as a lubricating medium, as a solvent for surface deposits, or as an occlusive film former, to coat the skin surface and to spread other ingredients in the emulsion on the skin.

The basic components of the emulsion are water, oil, and the modified polymer. A neutralizing agent is optionally used to adjust pH to the desired range. Since pH of the skin is about 5.5, it is desirable to adjust pH of topical skin compositions to approximately this pH. It is also possible to use primary surfactants to impart further stability of the emulsion, or to enhance performance attributes such as spreading or penetration of active ingredients, although the modified polymer can function by itself as a primary surfactant.

Suitable oil-in-water emulsions can be prepared in the usual manner. A stainless steel jacketed mixer can be used which is equipped with a suitable agitator. Deionized water is added to the mixer and the modified polymer is added thereafter while agitating the contents of the mixer. The modified polymer is preferably in powder form or it can be predispersed in mineral oil or mineral spirits. Once uniform dispersion is made of the modified polymer in water, oil and other components are added, one at a time with agitation. All of these steps can be carried out at room temperature.

Oil-in-water emulsions prepared in the manner described above, remained shelf-stable for over 12 months at ambient temperature and over 3 months at 50° C. Three months was the limit of the test, not the limit of stability at 50° C. When exposed to electrolyte in sufficient concentration, the emulsions display instantaneous break resulting in coalescence and release of the oil phase. The break characteristic of these emulsions can be easily achieved by the level of perspiration in normal skin.

The basic oil-in-water emulsion referred to herein comprises oil, modified polymer, water and other optional components such as neutralizing agents, perfuming agents, and the like. The emulsions contemplated herein are generally defined as follows, in weight percent:

|  | Broad | Preferred | Specific |
| --- | --- | --- | --- |
| Oil | 0.1–60 | 0.5–50 | 1–20 |
| Modified Polymer | 0.05–3 | 0.1–1 | 0.2–0.6 |
| Water |  | balance to 100% |  |
| pH | 3–10 | 3.5–9 | 4–8 |

Fully formulated topical skin compositions can be prepared with the oil-in-water emulsions disclosed herein by incorporating therein the desired components. Examples of cosmetic skin formulations which can be prepared with the emulsions include moisturizing lotions, barrier creams and lotions, cleansing creams and lotions, waterless hand cleaners, after-shave lotions, sunscreens, and the like.

One class of moisturizing lotions are based on emulsions of mineral oil, petrolatum, or lanolin oils. When these lotions are spread on skin, the oils form an occlusive layer which reduces the trans-epidermal loss of water, i.e., water loss from skin. The water thus retained in the stratum corneum in the skin then plumps the cells of the horny layer of the skin and thus mitigates the dry skin condition. The same benefits are not obtained when water is placed on the skin or when hands are immersed in water. When water is placed on the skin, it evaporates before it rehydrates the skin. Immersion of the skin in water often results in an abnormal degree of hydration of the stratum corneum, which is frequently accompanied by cellular damage. As a consequence, the stratum corneum loses its property as a moisture barrier, exacerbating the dry skin problem. The use of the oil-in-water emulsions disclosed herein in preparing moisturizing lotions offers extremely good spread of an oil layer on contact with the skin due to the fast-breaking of the emulsion. Furthermore, since the moisturizing lotion and other topical skin compositions referred to herein can be prepared with the modified polymer and without any of the conventional surfactants, the absence of surfactants in the oil layer results in a more effective barrier to trans-epidermal water loss.

Mineral spirits and mineral oil are used in preparing the stable and quick-breaking oil-in-water emulsions which form the basis for most of the various topical skin treating compositions. To identify these materials, a general description of mineral spirits and mineral oil is given herein.

One example of mineral spirits is a clear, combustible petroleum liquid product normally containing a major proportion of liquid aliphatic hydrocarbon materials. Specific gravity normally ranges from about 0.75 to about 0.81, with a boiling range from about 150° to about 220° C. While the flash point is normally above about 40° C., for safety reasons, the flash point should be above 60° C. A suitable mineral spirits composition contains 0 to 5% aromatics, about 40 to 80% paraffins, and about 15 to 60% naphtha. Such a composition has a flash point of about 60° C. Mineral oil is a liquid mixture of hydrocarbons obtained from petroleum having a specific gravity of 0.818 to 0.880.

Another example of mineral spirits is Stoddard solvent, a widely used dry-cleaning solvent. It is defined as a petroleum distillate which is clear and free of suspended matter and undissolved water, and free from rancid and objectionable odor. The minimum flash point is 100° F. with a distillation range of not less than 50% over at 350° F., 90% over at 375° F., and end point no higher than 410° F. Autoignition temperature thereof is 450° F.

Lanolin and petrolatum are also common ingredients in the compositions described herein. Lanolin is a derivative of the unctuous fat-like sebaceous secretion of sheep. Lanolin consists of a highly complex mixture of high molecular weight aliphatic esters, steroid or triterpenoid alcohols and fatty acids. Petrolatum is a semisolid mixture of hydrocarbons obtained from petroleum.

Typical moisturizing lotion base formulations of this invention are defined as follows, in weight percent:

|  | Broad Range | Preferred Range |
| --- | --- | --- |
| Mineral Oil | 1–40 | 2–25 |
| Modified Polymer | 0.05–1.0 | 0.1–0.5 |
| Water | balance to 100% by weight | |
| Neutralizing Agent | 0.01–2.00 | 0.05–1.0 |

The moisturizing lotion formulations can optionally contain other ingredients such as coemulsifiers or bodying agents, emollients, humectants, spreading agents, preservatives, and fragrances. Commonly used coemulsifiers or bodying agents include long chain alcohols such as cetyl, myristyl and stearyl alcohols which assist stabilization of the emulsion. Coemulsifiers are normally present in the range of 0.2 to 5%. Common emollients are mineral oil, petrolatum, lanolin and derivatives thereof, and alkyl triglycerides such as caprylic/capric triglycerides. Amount of emollient is usually in the range of 1 to 40%. Common humectants are glycerine, sorbitol, and other hydroscopic compounds, all of which at times are considered as emollients because of the water-retentive properties. Normal amounts of humectant varies from 1 to 10%. Common spreading agents include isopropyl myristate and cyclomethicone, which are normally used at a level of 0.1 to 3%. Common preservatives are the parabens and imidazolidinyl urea, which are used at a level of 0.05 to 0.5%. Any suitable fragrance can be used at a level of 0.1 to 2%. Amounts herein are based on the weight of the final formulation.

The same or similar optional ingredients can also be used in the same or similar amounts in barrier creams or lotions, cleansing creams or lotions, waterless hand cleaners, sunscreen lotions, after-shave lotions, and the like.

Barrier or protective hand-creams are used in the home and in the industry to protect skin which is subjected to abuse or insult by potential irritants. Barrier creams form a coherent, impervious, flexible, non-cracking film on the skin. Such products are usually sold in the form of lotions or creams which contain silicone oil. The use of the modified polymer in preparing stable and fast-breaking emulsions which are, in turn, used to make barrier creams or lotions, results in products which provide for a quick and an even spread of barrier oil over the entire skin surface. Adhesion of the barrier oil layer to the skin is enhanced and protection against irritants is increased since the cream or lotion vehicle can be devoid of surfactants which can cause partial re-emulsification of oil when the skin is immersed in water. Typical barrier cream or lotion base formulations of this invention are defined as follows, in weight percent:

|  | Broad Range | Preferred Range |
| --- | --- | --- |
| Mineral Oil | 0–50 | 0–30 |
| Silicone Oil | 0–50 | 0–30 |
| Modified Polymer | 0.05–1.0 | 0.1–0.5 |
| Neutralizing Agent | 0.01–2.0 | 0.05–1.0 |
| Water | balance to 100% | |

In the barrier cream or lotion formulations, the oil phase is normally a mixture of silicone oil and mineral oil but acceptable barrier formulations can be made with either mineral oil or silicone oil alone. However, all of the barrier formulations contain at least 1% and preferably at least 2% oil phase, whether mineral oil, silicone oil or mixture thereof.

The purpose of a cleansing cream or lotion is to remove facial make-up, skin surface grime, and oil from face and throat. Many modern cleansing creams are based on the solvent action of mineral oil on the oils and grease which bind either grime or make-up to the skin.

The properties desired in a good cleansing cream or lotion include emulsion stability and good cosmetic appearance, easy spreadability over the skin without too much drag, maintenance of lower viscosity on evaporation of the water, flushing of the skin and pore openings without absorption into the skin, and retention of a light emollient film on the surface of the skin after use. The emulsions stabilized with the modified polymer release oil on contact with the skin and exhibit quick cleansing action. Typical cleansing creams and lotions of this invention have the following base formulations, in weight percent:

|  | Broad Range | Preferred Range |
| --- | --- | --- |
| Mineral Oil | 1–40 | 5–25 |
| Modified Polymer | 0.05–2.0 | 0.1–1.0 |
| Neutralizing Agent | 0.01–5.0 | 0.05–2.5 |
| Preservative | 0.05–1.0 | 0.1–0.5 |
| Water | balance to 100% | |

Waterless hand cleaners are used for removal of heavy deposits of grease or tar from the hands. Lotion-type waterless cleaners are usually oil-in-water emulsions in which the oil is Stoddard's solvent or a similar type of mineral spirits. These products exhibit fast-break upon application to the hands which releases the oil phase. The oil phase, in turn, dissolves the grease or tar. The use of modified polymer in such products imparts shelf-stability with fast-break on application. Typical waterless hand cleaner base formulations of this invention are defined as follows, in weight percent:

|  | Broad Range | Preferred Range |
| --- | --- | --- |
| Mineral Spirits | 5–50 | 10–40 |
| Modified Polymer | 0.05–2 | 0.1–1.0 |
| Neutralizing Agent | 0.01–5 | 0.05–2.5 |
| Water | balance to 100% | |
| pH | 4–10 | 5–8 |

Waterless hand cleaners can also optionally contain pumice or other abrasive agents in amounts of 1 to 20%, and hydrophilic surfactants, such as alkylphenol ethoxylates or lauryl sulfates, in amounts of 0.5 to 5% to aid removal of grime and rinsing. These amounts are based on the weight of the final formulation.

Sunscreen lotions, such as those based on dioctyl para-amino benzoic acid, are very viscous oils which do not spread easily on the skin. Considerable formulation expertise is required to formulate sunscreen lotions which do not plate-out unevenly on the skin and which spread evenly on application. The fast-breaking, easy spreading lotions afforded by the primary emulsification with the modified polymer provides a vehicle which overcomes the prior art deficiencies. Typical sunscreen base formulations of this invention are defined as follows, in weight percent:

|  | Broad Range | Narrow Range |
| --- | --- | --- |
| Mineral Oil | 1–60 | 2–35 |
| Modified Polymer | 0.05–1 | 0.1–0.5 |
| Neutralizing Agent | 0.01–2 | 0.05–1.0 |
| Sunscreen Agent | 0.1–30 | 0.5–20 |
| Water | balance to 100% | |

Suitable sunscreen agents include methyl anthranilate, salicylic acid derivatives, cinnamic acid derivatives, p-amino-benzoic acid and its derivatives, benzal acetone derivatives, phenylacrylic derivatives, tannic acid derivatives, benzalazines, benzophenones, and alicyclic dienones.

After-shave lotions are used to deposit a light emollient film on skin after shaving it. These lotions are desirably fast-breaking oil-in-water emulsions which are applied by splashing onto the skin rather than rubbing it into the skin. The modified polymers deliver these attributes while also ensuring storage-stability of the lotion. Typical after-shave lotion base formulations of this invention are defined as follows, in weight percent:

|  | Broad Range | Narrow Range |
| --- | --- | --- |
| Mineral Oil | 0.1–20 | 0.5–10 |
| Modified Polymer | 0.01–1.0 | 0.05–0.5 |
| Neutralizing Agent | 0.01–2.5 | 0.02–1.25 |
| Water | balance to 100% | |

The modified polymer is prepared by polymerizing a preponderant amount of a carboxylic monomer and a lesser amount of a long chain acrylate ester. Amount of the carboxylic monomer can be in the range of 50 to 99% by weight, preferably 80 to 99% by weight, and especially 90 to 98% by weight whereas amount of the acrylate ester can be in the range of 1 to 50% by weight, preferably 1 to 20% by weight, especially 2 to 10% by weight. Amounts of the carboxylic monomer and the acrylate ester are based on the combined weight of both components. It should be understood that more than one carboxylic monomer and more than one acrylate ester can be used in the monomer charge.

The modified polymers can optionally be crosslinked by inclusion in the monomer charge of a suitable crosslinker in amount of about 0.1 to 4%, preferably 0.2 to 1% by weight based on the combined weight of the carboxylic monomer and the acrylate ester. The crosslinker is selected from polymerizable monomers which contain a polymerizable $CH_2=C<$ group and at least one other polymerizable group, the unsaturated bonds of which are non-conjugating with respect to each other.

Production of the copolymers of this invention employs a monomeric mixture which contains two essential monomeric ingredients, each in certain proportions, one being a monomeric olefinically-unsaturated carboxylic monomer of 3 to 6 carbon atoms and the other being an acrylic ester having a long chain aliphatic group. Optionally, there is included in the monomeric mixture a crosslinking monomer. Amount of the carboxylic monomer is generally in a major proportion whereas the acrylic ester is used in a minor proportion. In a preferred embodiment, amount of the carboxylic monomer is 80 to 99% but especially 90 to 98% by weight whereas amount of the comonomer is 20 to 1, especially 10 to 2 weight percent, based on the weight of the two monomers.

The copolymers of a carboxylic monomer and an acrylic ester having a long chain aliphatic group can have polymerized therein a major proportion of a lower alkyl ester of acrylic acid, such as ethyl acrylate, in amount of 0–40% by weight preferably 5–30%, based on the total monomer charge.

The carboxylic monomers useful in the production of the copolymers of this invention are the olefinically-unsaturated carboxylic acids containing at least one activated carbon-to-carbon olefinic double bond, and at least one carboxyl group, that is, an acid containing an olefinic double bond which readily functions in polymerization because of its presence in the monomer molecule either in the alpha-beta position with respect to a carboxyl group or as a part of a terminal methylene grouping. The anhydrides can also be used, especially maleic anhydride.

The preferred carboxylic monomers for use in this invention are the monoolefinic acrylic acids having the general structure

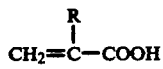

wherein R is a substituent selected from the class consisting of hydrogen, halogen, hydroxyl, lactone, lactam, and the cyanogen (—C≡N) groups, monovalent alkyl radicals, monovalent aryl radicals, monovalent aralkyl radicals, monovalent alkaryl radicals and monovalent cycloaliphatic radicals. Of this class, acrylic acid itself is most preferred because of its generally lower cost, ready availability, and ability to form superior polymers. Another particularly preferred carboxylic monomer is maleic anhydride.

The preferred acrylic ester monomers having long chain aliphatic groups are derivatives of acrylic acid represented by the formula:

wherein $R^1$ is selected from hydrogen, methyl and ethyl groups and $R^2$ is selected from alkyl groups having from 8 to 30 carbon atoms and oxyalkylene and carbonyloxyalkylene groups, preferably alkyl groups of 10 to 22 carbon atoms. The oxyalkylene and carbonyloxyalkylene groups are particularly oxyethylene and carbonyloxyethylene groups. Representative higher alkyl acrylic esters are decyl acrylate, lauryl acrylate, stearyl acrylate, behenyl acrylate and melissyl acrylate, and the corresponding methacrylates.

The modified polymers described herein, when tested in the form of 0.2% aqueous mucilages, have viscosity of 100 to 50,000 cps, preferably 250 to 40,000 cps, and especially 500 to 35,000 cps. In the form of 1.0% aqueous mucilages, have viscosity of 1,000 to 100,000 cps, preferably 2,000 to 90,000 cps, and especially 2,500 to 85,000 cps. These viscosities were measured using Brookfield RVT model viscometer at spindle speed of 20 rpm in the pH range of 7.2 to 7.6. The viscosity of these mucilages is an indication of the molecular weight of the herein-disclosed modified polymers which are characterized as being lightly crosslinked. Molecular weight of partially or fully crosslinked hydrophilic polymers of which a small portion is one or more hydrophobic moiety is difficult or impossible to determine.

The preferred crosslinking monomer, if one is employed, is a polyalkenyl polyether having more than one alkenyl ether grouping per molecule. The most useful possess alkenyl groups in which an olefinic double bond is present, attached to a terminal methylene grouping, $CH_2=C<$. They are made by the etherification of a polyhydric alcohol containing at least 4 carbon atoms and at least 3 hydroxyl groups. Compounds of this class may be produced by reacting an alkenyl halide, such as allyl chloride or allyl bromide with a strongly alkaline aqueous solution of one or more polyhydric alcohols. The product is a complex mixture of polyethers with varying numbers of ether groups. Analysis reveals only the average number of ether groupings on each molecule. Efficiency of the polyether crosslinking agent increases with the number of potentially polymerizable groups on the molecule. It is preferred to utilize polyethers containing an average of two or more alkenyl ether groupings per molecule.

The modified polymers are preferably made by polymerization in an inert diluent having some solubilizing action on one or more of the monomeric ingredients but substantially none on the resultant polymer. Polymerization in mass may be employed but is not preferred because of the difficulty in working up the solid polymeric masses obtained. Polymerization in an aqueous medium containing a water-soluble free radical catalyst peroxygen is useful, the product being obtained either as a granular precipitate or as a highly swollen gel, either of which may be used directly or are easily further sub-divided and dried.

Polymerization in an organic liquid which is a solvent for the monomers but a non-solvent for the polymer, or in a mixture of such solvents, in the presence of a solvent-soluble catalyst, is most preferred because the product is usually obtained as a very fine, friable and often fluffy precipitate which, after solvent removal, seldom requires grinding or other treatment before use. Suitable solvents for the latter method include benzene, xylene, tetralin, hexane, heptane, carbon tetrachloride, methyl chloride, ethyl chloride, bromo trichloro methane, ethyl acetate, dimethyl carbonate, diethyl carbonate, ethylene dichloride, and mixtures of these and other solvents.

Polymerization can also be carried out in an aqueous medium of a soluble nonredox multivalent inorganic salt. The acid is too soluble in plain water, therefore, the inorganic salt is added to insolubilize the acid. In this manner, another phase is introduced and the acid is polymerized in a suspension rather than in solution.

The aqueous medium can be a concentrated solution of the salt or it can be a salt slurry of the salt. The difference between the two is considerable. Whereas a concentrated solution of magnesium sulfate salt at reaction temperature is composed of about 2.5 weight parts of the salt per single weight part of water, a slurry of the salt is composed of about 20 weight parts of the salt per single weight part of water. The use of a concentrated salt solution as the reaction medium is preferred.

Although magnesium sulfate is the preferred salt, other organic salts or hydrates thereof can be used, including the nonredox multivalent ion salts such as potassium sulfate, calcium chloride, secondary sodium phosphate and salts employing combinations of anions and cations such as aluminum, barium, beryllium, cadmium, calcium, chloride, chromium, cobalt, lead, magnesium, manganese, molybdate, nickel, selenate, strontium, sulfate, tin tungsten, zinc, and the like.

Success of this polymerization method depends on the fact that the polymerization reaction takes place in discrete and separate oil-in-water droplets. Therefore, water solubility of the inorganic salt employed should be at least about one-half molar in order to salt out the monomer and the formed water-soluble polymer. Moreover, the readily soluble salts can be readily washed out of the finished polymer.

Polymerization in the diluent medium is carried out in the presence of a free radical catalyst in a closed vessel in an inert atmosphere and under autogenous pressure or artificially-induced pressure or in an open vessel under reflux at atmospheric pressure. Temperature of the polymerization may be varied from 0° to 100° C. depending to a large degree on the molecular weight desired in the polymer. Polymerization under reflux at 50° to 90° C. under atmospheric pressure using a free radical catalyst is generally effective in bringing a polymer yield of 75% to 100% in less than 10 hours.

Suitable polymerization catalysts include peroxygen compounds such as sodium, potassium and ammonium persulfates, caprylyl peroxide, benzoyl peroxide, hydrogen peroxide, pelargonyl peroxide, cumene hydroperoxides, tertiary butyl diperphthalate, tertiary butyl perbenzoate, sodium peracetate, sodium percarbonate, and the like, as well as azo diisobutyryl nitrile, hereinafter referred to as azoisobutyronitrile. Other catalysts utilizable are the so-called "redox" type of catalysts and the heavy-metal activated catalyst systems.

These modified polymers generally do not attain their maximum properties in water until converted to a partial alkali, ammonium or amine salt. The neutralizing agent is preferably a monovalent alkali such as sodium, potassium, lithium or ammonium hydroxide or the carbonates and bicarbonates thereof, or mixtures of the same, and also amine bases having not more than one primary or secondary amino group.

Conventional oil-in-water emulsions have particle size of less than 10 microns, preferably 0.1–5 microns. Surprisingly, the oil-in-water emulsions can be prepared with the modified polymer having a much larger particle size averaging about 50 microns and are in the range of 10 to 100 microns.

The modified polymers, which contain a small proportion of long chain acrylate esters, can function as primary emulsifiers or surfactants whereas polymers similar to the modified polymers but devoid of long chain acrylate esters do not possess this property. Although it is alleged in the prior art that polyacrylic acids partially neutralized with long chain alkylamines are capable of behaving as primary emulsifiers, such polyacrylic acids, when used to prepare the emulsion, yield emulsions which are stable only at high pH values above about 6 whereas the emulsions prepared with the modified polymer containing long chain acrylate monomers are stable at low pH of about 3 to 6. The emulsions prepared with a modified polymer have a large droplet size, as already noted, and they display quick break when applied to skin.

It is interesting to note that similar polymers which are devoid of a long chain acrylic monomer do not have properties of the modified polymers. For instance, the various acrylic acid homopolymers, when used to prepare oil-in-water emulsions, do not form stable emulsions and the resulting emulsions do not have the quick breaking property. Examples of such homopolymers are Carbopol® 934, 940 and 941 resins which are lightly crosslinked polyacrylic acids prepared in benzene solvent and having respective estimated molecular weights of 3.0 million, 4.0 million and 1.25 million. When these resins were used in making oil-in-water emulsions, the resulting emulsions were not shelf-stable. In terms of shelf stability, these emulsions devoid of emulsifiers were only stable for less than one week at room temperature. It is essential to include conventional emulsifiers in the prior art emulsions to render them stable, however then they do not have the quick breaking property. The emulsions of the present invention have both stability and quick breaking property in absence of conventional emulsifiers.

The Examples that follow demonstrate the herein-disclosed invention as it relates to preparation of stable and quick break oil-in-water emulsions and the use of such emulsions in topical skin compositions.

EXAMPLE 1

This example demonstrates preparation of a modified acrylic acid polymer containing a small amount of a long chain alkyl acrylate.

In a representative embodiment to demonstrate the preparation of the modified polymer, 1100 grams of benzene was charged to a stirred reactor equipped with a marine type agitator. Then 250.28 grams of acrylic acid, 5.72 grams of stearyl methacrylate and 0.858 grams of allyl pentaerythritol were added to the reactor and the measuring vessel rinsed with 200 grams of benzene, which was added to the reactor. The reactor was heated to 78° C. and purged with 2 ft$^3$/hour of nitrogen for 30 minutes. Then 0.4 gram of lauryl peroxide in 50 grams of benzene was added to the reactor and the measuring vessel was rinsed with 50 grams of benzene that was added to the reactor. The polymerization reaction was allowed to run for 5 hours while controlling the temperature at 80° to 81° C. At the end of this period, the polymer was dried at 100° C. in a Roto-evaporator. The resulting polymer was added to 500 ml of distilled water and neutralized to pH 7 with 18 percent aqueous sodium hydroxide.

EXAMPLE 2

This example demonstrates preparation of an oil-in-water emulsion using the modified polymer of Example 1.

Pursuant to the usual procedure, the emulsion was prepared by placing 85 weight parts of cold deionized water into a stainless steel jacketed kettle equipped with lightning agitation. The modified polymer of Example 1 in powder form in amount of 0.5 weight part was sprinkled into the water with rapid agitation. Agitation was continued for about one half hour until a uniform dispersion of the modified polymer in water was obtained. Then, 14 weight parts of mineral oil was added to the kettle with rapid agitation followed by 0.2 weight part of triethanolamine neutralizing agent. Agitation was continued for about another one half hour until a uniform emulsion was formed.

The resulting emulsion was oil-in-water having droplet size of about 20 to 60 microns and pH of about 5. It was stable for more than 24 months at room temperature and when applied to skin, broke instantaneously on contact, releasing oil.

EXAMPLE 3

This experiment demonstrates preparation of a moisturizing lotion base using the stable and quick-breaking oil-in-water emulsion described herein.

Pursuant to the normal procedure, a moisturizing lotion was prepared from the following ingredients given in weight parts:

| | |
|---|---|
| Deionized Water | 88.90 |
| Modified Polymer of Ex. 1 | 0.60 |
| Mineral Oil, 65/75 cps. | 10.10 |
| Triethanolamine, 99% | 0.50 |

This composition was prepared by sprinkling powdered modified polymer into water in a mixer while agitating water for about one half hour until a uniform dispersion was formed. This was followed by addition of mineral oil with agitation and the neutralizing agent. Initial pH of the emulsion was 5.93, its viscosity was 23,200 cps at 25° C., and it had good stability. When applied to skin, the moisturizing composition broke instantaneously on contact with the skin.

EXAMPLE 4

A moisturizing lotion was prepared using the following ingredients, given below in weight parts:

| Water Phase | |
|---|---|
| Water | 84.8 |
| Modified Polymer | 0.4 |
| Glycerin | 5.0 |
| Propylene Glycol | 1.0 |
| Methyl Parabens | 0.2 |
| Propyl Parabens | 0.1 |
| Oil Phase | |
| Mineral Oil | 5.0 |
| Cetearyl Alcohol | 1.0 |
| Glycol Stearate | 1.0 |
| Cetyl Acetate | 0.25 |
| Acetylated Lanolin Alcohol | 0.35 |
| Dimethicone | 0.50 |
| Neutralizers | |
| Triethanolamine (TEA) | 0.4 |
| Fragrance | as required |

Procedure

The procedure involved the dispersion of the modified polymer in water in a mixer and the addition thereto of the remaining water phase ingredients with mild agitation. Separately, the oil phase ingredients were combined and heated to 70° C. Then the heated oil phase was added to the ambient temperature water phase with agitation until a uniform dispersion was obtained. The neutralizing agent (TEA) was then added with continued agitation while the emulsion was cooled to 40° C. The fragrance was added last prior to terminating agitation. The emulsion was then allowed to cool to room temperature.

This emulsion was storage-stable and broke instantaneously when applied to skin.

This creamy, smooth lotion had an oil rich appearance without a heavy, greasy feel. The modified polymer gave a rich feel, yet quick rub-in for desired moisturizing with a spreading occlusive barrier on the skin.

EXAMPLE 5

A barrier cream was prepared using the following ingredients, given below in weight parts:

| Deionized water | 78.9 |
|---|---|
| Modified Polymer of Ex. 1 | 0.4 |
| Mineral Oil, 65/75 cps | 10.0 |
| Silicone, 96-200 cps | 10.0 |
| Perfume | 0.5 |
| Triethanolamine, 99% | 0.2 |
| Total | 100.0 weight parts |

The above barrier cream was prepared in a stainless steel mixer by sprinkling the modified polymer powder into rapidly agitated cold water until a uniform dispersion was obtained. Then, mineral oil and silicone oil were added one at a time with agitation, followed by addition of perfume and the neutralizing agent, one at a time, to the reactor with agitation. All of this was done at room temperature.

The barrier cream described above was stable and broke instantaneously on coming in contact with the skin. When applied to the skin, the barrier cream rendered the skin surface so hydrophobic that water readily beaded on the skin surface.

EXAMPLE 6

A cleansing lotion was prepared by mixing the following components, given in weight parts:

| Water | 78.2 |
|---|---|
| Modified Polymer of Ex. 1 | 0.2 |
| Cetyl Alcohol | 0.5 |
| Caprylic/Capric Triglyceride | 2.0 |
| Mineral Oil | 13.0 |
| PEG-8 | 0.5 |
| Triethanolamine | 0.4 |
| Imidazolidenyl Urea | 0.3 |
| Methyl Paraben | 0.1 |

In the above cleansing cream, mineral oil and the triglyceride provide the solvent action, imidazolidinyl urea was a preservative, cetyl alcohol was a bodying agent or a secondary emulsifier, methyl paraben was methyl p-benzoic acid which functioned as a preservative, triethanolamine was a neutralizing agent, and the modified polymer functioned to impart stability during storage of the lotion and quick break of the cleansing lotion when applied to the skin. PEG-8 was polyethylene glycol having an average of 8 ethoxy groups per molecule. PEG-8 functioned as a lubricant and humectant.

The above cleansing lotion was a stable emulsion, had pH of 5.6 and viscosity of 5100 cps at 25° C.

EXAMPLE 7

A waterless hand cleaner was prepared from the following components given in weight parts:

| | Prior Art Cleaner | Inventive Cleaner |
|---|---|---|
| Mineral Spirits | 30.0 | 30.0 |
| Surfactant | 2.0–5.05 | |
| Lanolin | 5.0–15.0 | 10.0 |
| Pumice | 5.0 | 5.0 |
| Polymer | 1.0 | 0.3 |
| Triethanolamine | 1.0 | 0.6 |
| Water | to 100% | 54.1 |
| Total | | 100.0 |

Preparation of the waterless hand cleaner of this invention was characterized by ease of handling, production time of about one-half, and a stable emulsion with coarse or large droplets. Ease of handling resulted from the fact that the modified polymer was used in the form of a high solids dispersion in mineral spirits (44% solids). The resulting emulsion had quick break, good cleansing properties, and was stable on storage.

Preparation of the inventive cleaner was made with a modified polymer described above whereas the prior art cleaner was prepared with a homopolymer of acrylic acid, i.e., a lightly crosslinked Carbopol ® 934 resin. Preparation of the prior art waterless cleaning composition was accompanied with difficulties in dispersing powdered Carbopol ® 934 resin. The prior art cleaner composition was characterized by an emulsion of fine particles which had good cleansing properties but experienced reduction in viscosity and, in some cases, emulsion separation, on storage, indicating an unstable emulsion.

EXAMPLE 8

A sunscreen lotion was prepared by mixing the following ingredients, which are given in weight parts:

| | |
|---|---|
| Water | 79.6 |
| Mineral Oil | 10.0 |
| Dioctyl p-Aminobenzoic Acid | 10.0 |
| Modified Polymer of Ex. 1 | 0.4 |
| Triethanolamine | 0.2 |

The above sunscreen lotion was prepared by sprinkling the modified polymer of Example 1 into rapidly agitated cold water until a uniform dispersion was obtained. Di-octyl p-aminobenzoic acid was dissolved in the mineral oil and this oil phase was added to the aqueous polymer dispersion and mixed until a homogeneous dispersion of the oil in the aqueous phase was obtained. At this point, the neutralizing agent, triethanolamine, was added and the lotion was mixed until a homogeneous emulsion was obtained.

The product exhibited good emulsion stability during storage and broke immediately upon application to the skin to spread a uniform layer of oil containing sunscreen agent over the area of application.

EXAMPLE 9

An after-shave lotion was prepared by mixing the following ingredients, which are given in weight parts:

| | |
|---|---|
| Water Phase | |
| Water | 90.4 |
| Modified Polymer of Ex. 1 | 0.2 |
| Glycerin | 2.5 |
| Hydrogenated Starch Hydrolysate | 2.5 |
| DMDM Hydantoin | 0.3 |
| Oil Phase | |
| Mineral Oil | 2.0 |
| Isopropyl Palmitate | 2.0 |
| Fragrance | q.s. |
| Neutralizers | |
| TEA | 0.1 |

The modified polymer was dispersed into water with rapid agitation. Thereafter, the remaining water phase ingredients were added with mild agitation. The oil phase ingredients were combined and added to the water phase with rapid agitation at ambient temperature. Agitation was continued until a uniform emulsion was obtained. At this point, triethanolamine was added as neutralizer. The product was storage stable, but broke instantaneously on application to the skin to release the emollients.

In the above formulation for an after-shave lotion, hydrogenated starch hydrosylate functioned as a humectant; DMDM hydantoin was a preservative; and isopropyl palmitate functioned as an emollient and as a spreading agent.

EXAMPLE 10

This example demonstrates preparation of two stable and quick-breaking emulsions using a modified polymer which was a copolymer of ethyl acrylate, methacrylic acid and 0.5–25% by weight of a long chain acrylate ester, i.e., alkyl poly(oxyethylene) poly(carbonyloxyethylene)acrylate, as disclosed in U.S. Pat. No. 4,421,902. The composition of each emulsion was as follows, in weight parts:

| | Emulsions | |
|---|---|---|
| | A | B |
| Modified Polymer | 3.0 | 3.0 |
| Mineral Oil | 20.0 | — |
| Silicone Oil | — | 20.0 |
| Deionized Water | 76.7 | 76.7 |
| Triethanolamine | 0.3 | 0.3 |
| Total | 100.0 | 100.0 |
| pH | 7.0 | 7.0 |
| Br. Viscosity @ 20 rpm, cps | 16,500 | 15,000 |

The above emulsions were stable and exhibited the fast break character, however, the above emulsions were stable only above pH of 6.5. The modified polymer used in preparing the above emulsions does not exhibit any significant thickening property below pH of 6.5 in aqueous solutions.

What is claimed is:

1. A storage-stable oil-in-water emulsion composition comprising water, oil, and a lightly crosslinked modified polymer wherein in said emulsion, water forms the continuous phase and oil forms the discontinuous phase in the form of oil droplets dispersed in the water, said modified polymer is a copolymer having a major portion of a monoolefinically unsaturated carboxylic acid monomer or its anhydride of 3 to 6 carbon atoms and a minor portion of a long chain acrylate or methacrylate ester monomer, said emulsion having the characteristic of breaking quickly on contact with an electrolyte, wherein said modified polymer defines a viscosity of 100 to 50,000 cps when measured in the form a 0.2 weight percent aqueous mucilage at pH of about 7.2 to 7.6, and wherein the components of said composition are given below in weight parts:

| | |
|---|---|
| Mineral Oil | .1 to 60 |
| Modified Polymer | .05 to 3 |
| Water | 45 to 100. |

2. The composition of claim 1 wherein the major portion of the modified polymer is an acid monomer selected from the group consisting of maleic anhydride, and acid monomers defined as follows:

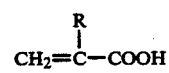

where R is selected the group consisting of from hydrogen, halogen, hydroxyl, lactone, lactam, and cyanogen ($-C\equiv N$) groups, and monovalent alkyl, aryl, aralkyl, alkaryl, and cycloaliphatic groups; and wherein the minor portion is an ester comonomer defined as follows:

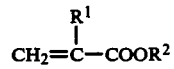

where $R^1$ is selected from the group consisting of hydrogen, methyl, and ethyl groups and $R^2$ is selected from alkyl groups of 8 to 30 carbon atoms.

3. The composition of claim 2 wherein the amount of the unsaturated acid or its anhydride is 80 to 99% by weight and amount of said ester monomer is 20 to 1% by weight, based upon the weight of the modified polymer.

4. Composition of claim 3 wherein the acid monomer is selected from the group consisting of acrylic acid, methacrylic acid, and mixtures thereof and said ester monomer is selected from the group consisting of acrylate esters where $R^1$ is selected from the group consisting of hydrogen and methyl groups and $R^2$ is selected from the group consisting of alkyl groups of 10 to 22 carbon atoms.

5. Composition of claim 4 wherein said composition is devoid of a primary surfactant and wherein the composition is stable at pH of about 3 to about 6, and said modified polymer has a viscosity of 100 to 50,000 cps when measured in the form of a 0.2% aqueous mucilage at pH of 7.2–7.6.

6. Composition of claim 5 wherein the amount of oil is 0.5 to 50 parts, and the amount of said modified polymer is 0.1 to 1 part.

7. Composition of claim 6 wherein the amount of oil is 1 to 20 parts and the amount of said modified polymer is 0.2 to 0.6 parts.

8. Composition of claim 7 wherein the composition is shelf-stable at about 20° C. for at least one year.

9. Composition of claim 2 further comprising a sunscreen agent in an amount of about 0.5 to 20 weight parts based upon total weight of the composition.

10. Composition of claim 9 wherein the sunscreen agent is diocytl p-amino benzoic acid.

* * * * *